United States Patent
Wulfsberg et al.

[11] Patent Number: 5,999,344
[45] Date of Patent: Dec. 7, 1999

[54] ENDOSCOPIC TELESCOPE WITH ROD LENSES SPACED BY SPACER TUBES

[75] Inventors: Jens Peter Wulfsberg, Neritz; Holger Frische, Jesteburg; Michael Weber, Hamburg, all of Germany

[73] Assignee: Olympus Winter & Ibe GmbH, Hamburg, Germany

[21] Appl. No.: 09/150,852

[22] Filed: Sep. 10, 1998

[30] Foreign Application Priority Data

Sep. 26, 1997 [DE] Germany ............... 197 42 454

[51] Int. Cl.⁶ .................. G02B 7/02; G03B 13/06
[52] U.S. Cl. .................. 359/819; 359/362; 359/434
[58] Field of Search .................. 359/362, 434–435, 359/819, 820

[56] References Cited

U.S. PATENT DOCUMENTS 4,303,306 12/1981 Ookawa .................. 359/819
5,020,893 6/1991 Karst et al. .................. 359/435

FOREIGN PATENT DOCUMENTS 1 127 112    4/1962   Germany.
34 31 631    3/1986   Germany.
3-109521     5/1991   Japan .................. 359/819

*Primary Examiner*—Thong Nguyen
*Attorney, Agent, or Firm*—Walter C. Farley

[57] ABSTRACT

An endoscopic telescope has a system tube in which spacer tubes are alternatingly stacked with rod lenses each having an external diameter smaller than the inside diameter of the system tube and which have convex end faces supported against the axial ends of the spacer tubes. An end of at least one of the spacer tubes protrudes axially at an angle and at a rotational position so that it abuts the adjacent convex surface of a rod lens, thereby tilting the rod lens relative to the system tube axis. The spacer tubes and the rod lenses are mounted spring loaded between end holding devices in the system tube.

4 Claims, 3 Drawing Sheets

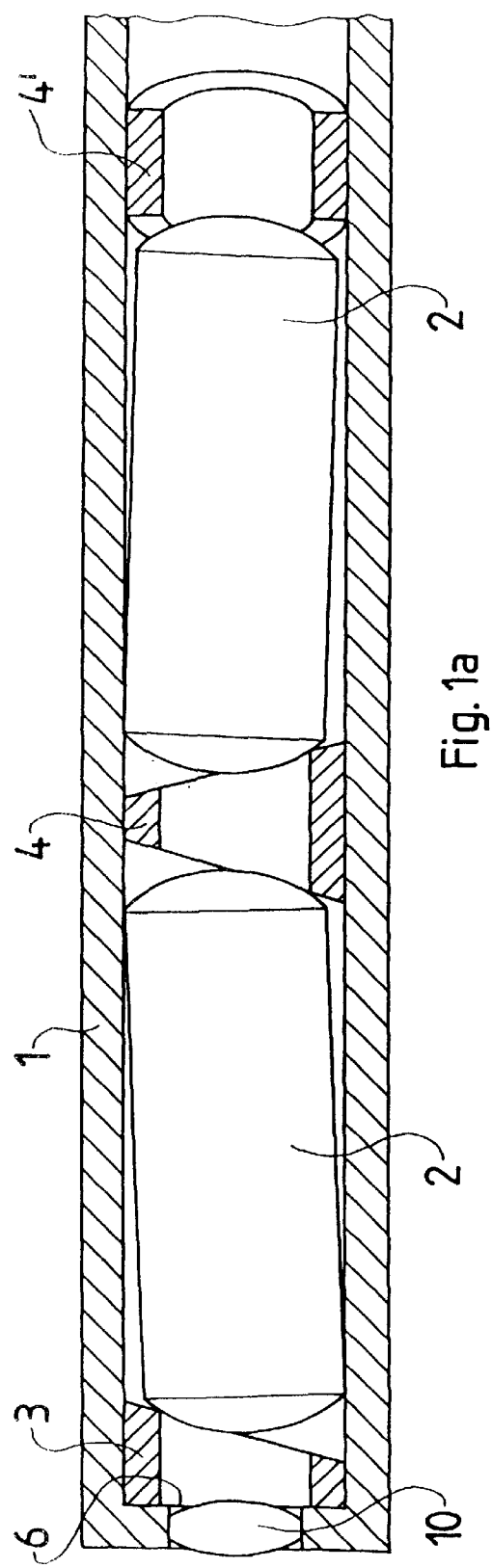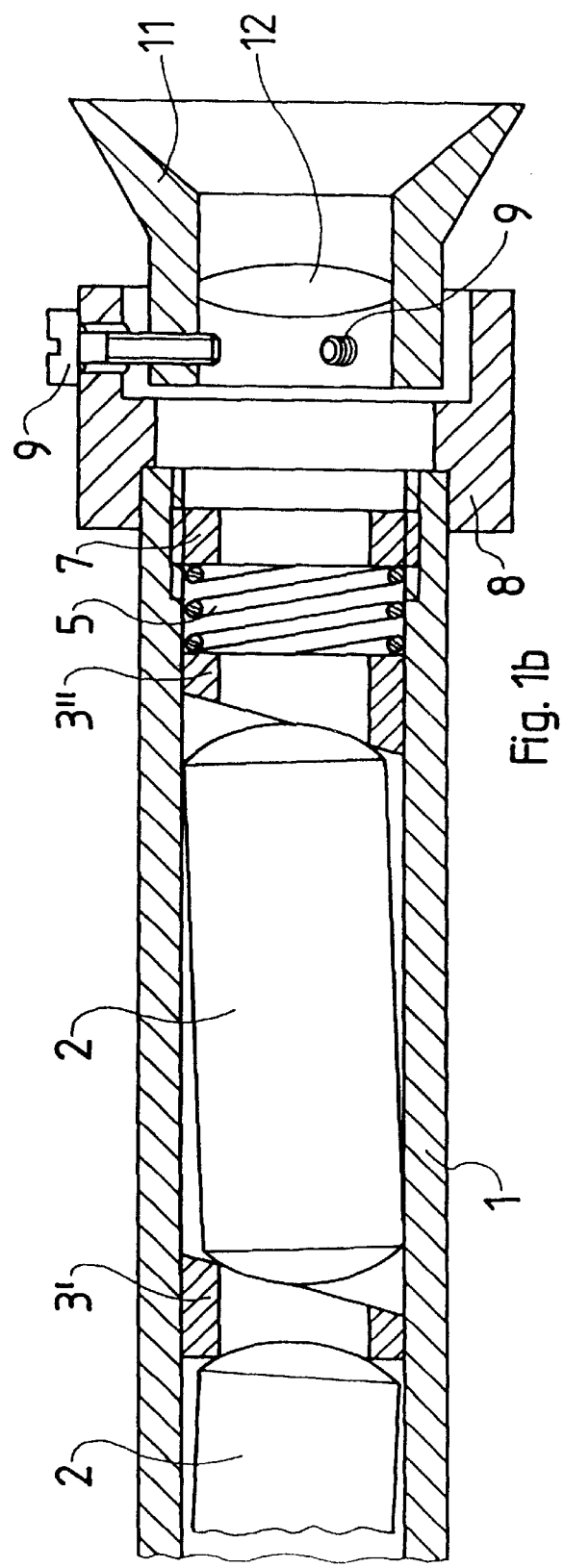

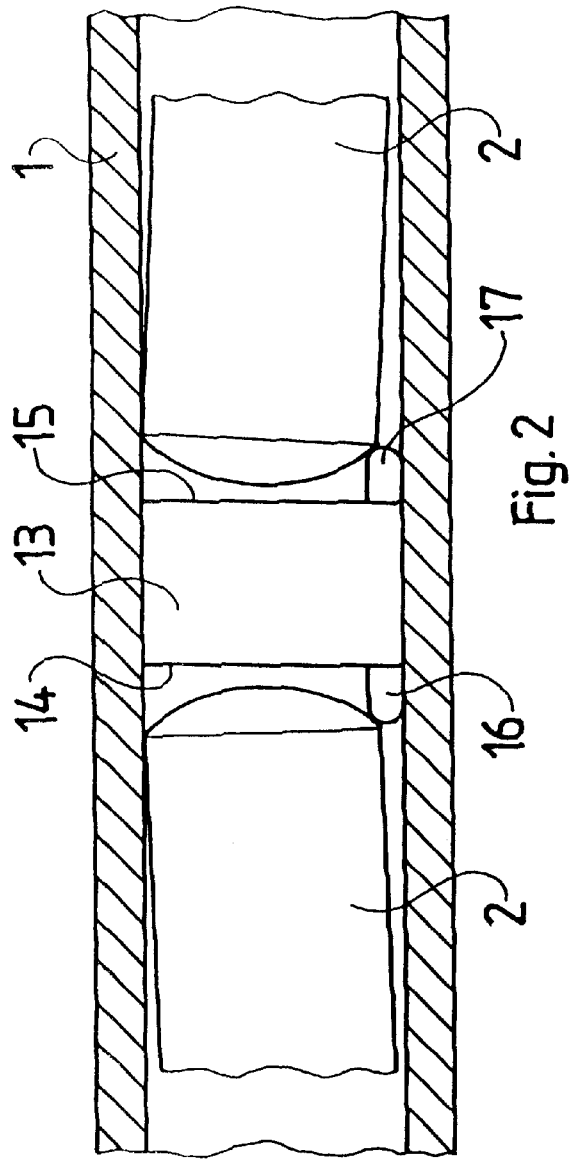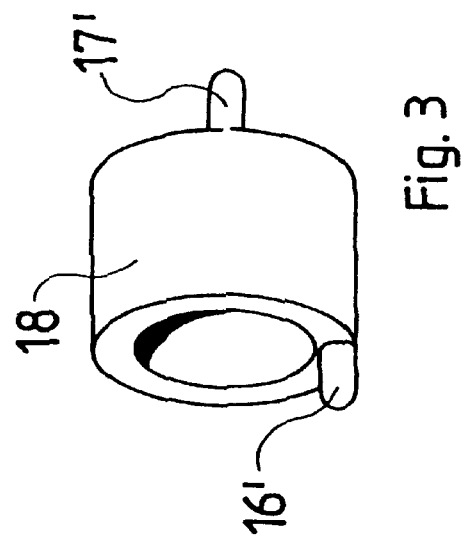

ENDOSCOPIC TELESCOPE WITH ROD LENSES SPACED BY SPACER TUBES

FIELD OF THE INVENTION

This invention relates to an endoscopic telescope having a system tube in which spacer tubes are stacked alternating with rod lenses that have an external diameter smaller than the inside diameter of the system tube, and which are supported at the axial ends of the spacer tubes with convex end faces.

BACKGROUND OF THE INVENTION

An endoscopic telescope of this general type is familiar from patent DE 34 31 631 C2, FIG. 2, wherein rod lenses are alternately stacked with spacer tubes in a system tube. As can be known in principle from patent DE - AS 11 27 112, the stack can be held in restraint by spring loading between the end holding devices of the system tube.

In the design shown in the first referenced document, the exterior diameter of the rod lenses is smaller than the inside diameter of the system tube so as to reduce the danger of breaking the lenses when bending the tube. The exterior diameter of the spacer tubes also is usually chosen to be smaller than the inside diameter of the system tube as well, so that the spacer tubes, as also the lenses, can slide easily within the system tube. This facilitates assembly of the system and assures that the stack which is formed from the lenses and the spacer tubes will be securely held together by spring resistance in the axial direction so that the bedding of the tube lenses in the system tube is free from play.

In the event of shock (for example, shaking when the endoscope optics system falls down), the clearance between the system tube and the lenses that is necessarily present at the side results in a lateral tilting of the lenses which shall hereinafter be described as "skipping." This skipping gives rise to an unintended and detrimental change in the viewing direction.

In the familiar design referred to initially, the rod lenses are gripped at their ends by flanges jutting out in a line to the axis from the axial ends of the spacer tubes and revolving around their whole circumference so as to prevent any tilting of the tube lenses. A certain degree of assembly play has to be preserved even between these flanges and the rod lenses, however, so that a little skipping is still possible even in the case of this familiar design. Providing the spacer tubes with circumferential flanges, which requires work on a turning lathe, is very expensive, however, given the small size of the spacer tubes.

SUMMARY OF THE INVENTION

An object of the invention is to provide an endoscopic telescope that reliably prevents skipping of the tube lenses, while using a more cost effective design.

The endoscopic telescope made in accordance with the invention makes use of spacer tubes which are designed to jut out asymmetrically in the direction of the axis on at least one side. By means of the resilience of the spring placed on the end of the stack of lenses, the whole stack of lenses along with the spacer tubes arranged between them is compressed in the line of the axis. As a result, the convex surface of one lens is brought to rest on the projecting part of one spacer tube. In this way, the resilience of the spring working axially on the stack of lenses is divided into two components. One of the components continues to work as the force of pressure in an axial direction. The second component, which results from the fact that the projecting part of the spacer tube is resting off-center on the convex fore-part of the tube lens, works cross-wise to the direction of the axis of the stack of lenses and presses the adjacent end of the tube lens laterally in the direction of the system tube until it comes to rest against the system tube. Through intentional tilting, then, there results a stable seating of the lens that is free from play and that excludes any possible movement of the lens. Any skipping of the viewing direction because of changes in the seating of the lens is thus effectively precluded. Even possible play between the spacer tube and the system tube is forestalled by means of the power component that is exerting its force crosswise to the axis of the system tube. The shifting of the viewing direction which, in this case, arises as a result of the deliberate tilting of the lens can be brought into balance by means of the usual control devices present on endoscope optics—those, for example, which are located on the eyepiece. The arrangement described above makes it possible to be able to use simply designed components and to be able to make do without the need for expensive, specially manufactured products. Even the simple kind of assembly—i.e., the familiar "filling up" of the system tube with lenses and spacer tubes—can be retained. As previously, security against breaking a lens is guaranteed by the fact that the lenses are spaced a distance from the system tube almost everywhere in the system tube, and by the possible give of the spring in the event of any bending of the system tube.

Advantageously, the spacer tube is designed to protrude on both sides. In this way the ends of the two rod lenses lying adjacent to a spacer tube are tilted crosswise to the direction of the axis of the system tube. An additional advantage of this embodiment of the invention lies in the fact that one need not worry about the alignment of the spacer tube during the usual "filling up" of the system tube with lenses and spacer tubes.

It is considered advantageous to provide protruding sides on all of the spacer tubes used in the system tube. This prevents any possible change in the bedding or seating of all the lenses located in the stack of lenses in the system tube as a result of sudden accelerations. It also prevents any skipping of the viewing direction for the endoscopic telescope.

It is also advantageous to make the protruding side of the spacer tube plane and inclined relative to its axis. This type of embodiment of the invention represents the simplest and thus most economical option for manufacturing spacer tubes which have the previously described advantages. Conventional spacer tubes or their semi-finished variants can be used for the manufacturing process. Only one side of the spacer tube has to be beveled, however. Also advantageous in this connection is the embodiment of the invention that has two beveled sides as mentioned above.

BRIEF DESCRIPTION OF THE DRAWINGS

The invention is described by way of example with reference to schematic illustrations thereof in the accompanying drawings wherein:

FIG. 1a is a longitudinal section taken along the central axis of an endoscopic telescope in accordance with the invention at one of its end areas with two embodiments of spacer tubes;

FIG. 1b is an axial. longitudinal section of the endoscopic telescope of FIG. 1a at its other end area;

FIG. 2 is a longitudinal axial section of a portion of an endoscopic telescope in accordance with the invention with a third style of spacer tube;

FIG. 3 is a perspective view of a modified form of a spacer tube of the embodiment illustrated in FIG. 2;

DESCRIPTION OF PREFERRED EMBODIMENTS

Figure 4:
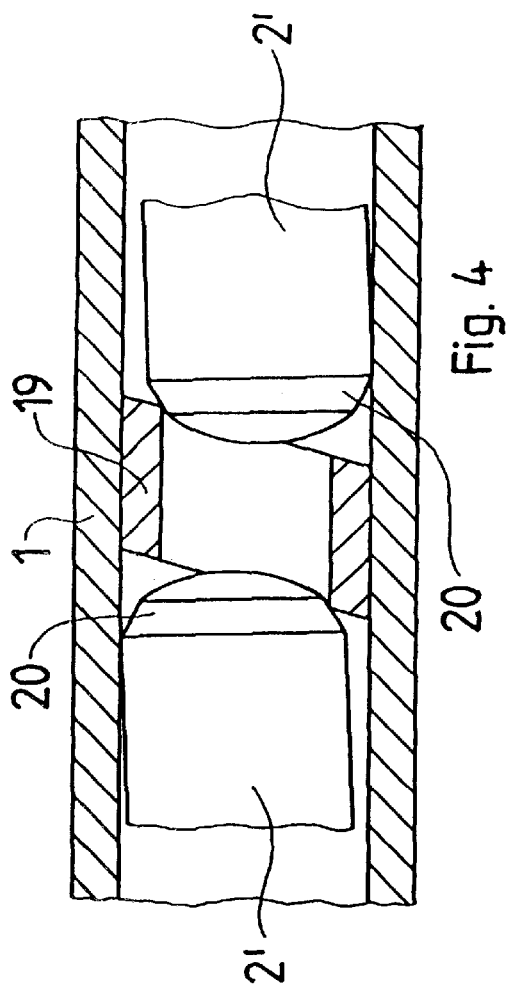
FIG. 4 is a longitudinal section in accordance with FIG. 2 with a fourth embodiment of spacer tube and with a different type of rod lens.

An endoscopic telescope with a system tube 1 in accordance with the invention is shown in FIGS. 1a and 1b. Several rod lenses 2 are arranged in system tube 1; for reasons of graphical simplicity, all of these rod lenses are presented as being identical and are drawn in an exaggerated way in this example of an embodiment according to the invention. Rod lenses 2 are separated and kept spaced apart by spacer tubes 3, 3', 3", 4 and 4', each of which in the case of spacer tubes 3, 3' and 3" has a straight end and a beveled end at the axial ends, and, in the case of spacer tubes 4 and 4', has two oppositely beveled ends.

Spacer tubes 3, 3' and 3" are shaped identically with each other. Spacer tube 3 is urged against a limit stop 6 in the front end area of the endoscopic telescope by the force of a spring 5 urged against the stack of lenses in the axial plane. Limit stop 6 carries an objective lens 10.

Spacer tube 3' lies between two rod lenses 2. Spacer tube 3" finally lies rotated axially and radially by 180° compared to spacer tubes 3 and 3 between a rod lens 2 and spring 5, which spring presses axially against a retaining ring 7 that is screwed into system tube 1 at the rear end area of the telescope.

Spacer tubes 4 and 4' are likewise identical as regards their shape and type. Spacer tube 4' lies opposite spacer tube 4, rotated radially by 90°, in system tube 1.

In the rear end area of the telescope and firmly attached to system tube 1 is a flange 8 in which is seated an adjustable eyepiece 11 with a lens 12, eyepiece 11 being held by means such as screws 9. Three screws 9 are typically inserted radially and angularly separated by 120° on the periphery of flange 8 to support eyepiece 11.

It can be seen in both Figures how the rod lenses 2 with their ends are urged laterally against system tube 1 by the beveled ends of spacer tubes 3, 3', 3", 4 and 4'. In this way there results stable seating of rod lenses 2 that is free from play and which also cannot be altered as a result of sudden accelerations.

At this juncture it is noted that the tilting of rod lenses 2 in the system tube 1 is shown in a very exaggerated fashion in the drawings.

The shifting of the viewing direction resulting from the deliberate tilting of rod lenses 2 can be corrected with the aid of eyepiece 11 which is adjustable using the screws 9.

A spacer tube 13 for separating two rod lenses 2 is placed in system tube 1 in the telescope according to the invention shown in FIG. 2. Axial ends 14 and 15 of spacer tube 13 are designed so as to be straight (i.e., perpendicular to the axis of system tube 1) and parallel to each other. Noses 16 and 17 protrude in parallel with the system tube axis from opposite axial faces. These noses generate cross force components by means of the axial power effect of a spring that is not shown in the drawing, and these cross force components press the adjacent ends of the rod lenses 2 laterally against system tube 1. In the embodiment shown, the noses 16 and 17 are aligned parallel with the axis.

FIG. 3 shows a spacer tube 18 which differs in its design from spacer tube 13 in FIG. 2 only by circularly displaced noses 16' and 17'—in this case, for example, offset by 90°. With this embodiment, lenses 2 in the stack of lenses arrange themselves so that they are tilted differently.

FIG. 4 shows a spacer tube 19 located in a system tube 1. Both axial ends of spacer tube 19 are formed to slant at an angle relative to the system tube axis. In contrast to the embodiments of FIGS. 1a and 1b, here the two ends are formed with bevels that are parallel to each other. In addition to this, this figure also shows that even rod lenses 2'with bezels 20 can be engaged by the spacer tubes so that the lenses tilt laterally.

Figure 5:
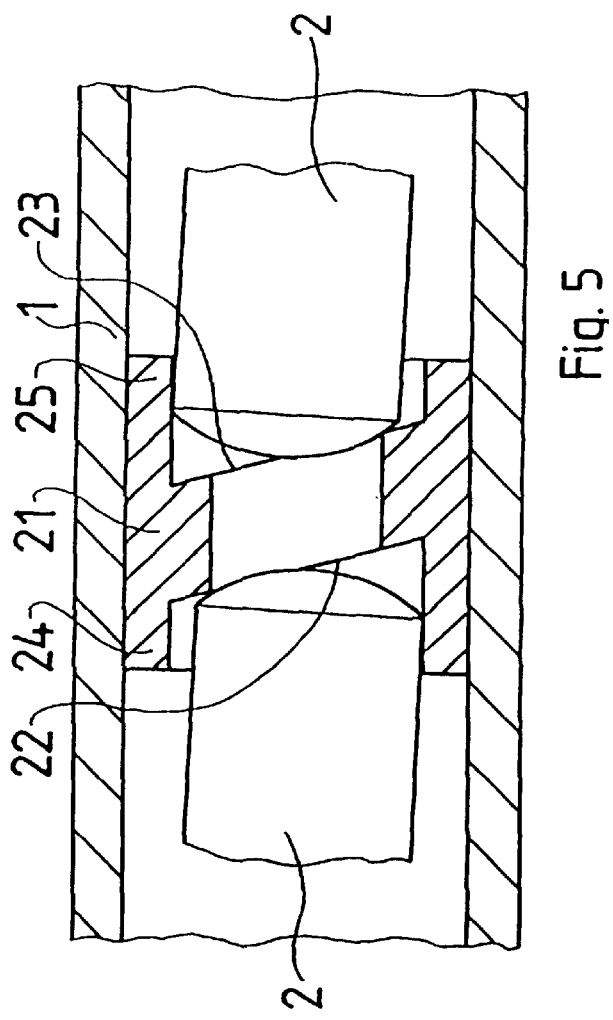
FIG. 5 is a longitudinal section showing a fifth embodiment of spacer tube.

FIG. 5 shows a further embodiment of spacer tube of a telescope in accordance with the invention. A spacer tube 21 separating two rod lenses 2 in system tube 1 has tubular extensions 24 and 25 that extend parallel with the system tube axis beyond the axial extensions of axially facing ends 22 and 23 of spacer tube 21. The inside diameter of these extensions 24 and 25 is nevertheless larger than the exterior diameter of the rod lenses 2 that are used.

In this way the previously described transverse force components press the ends of rod lenses 2 against the interior walls of tubular extensions 24 and 25 of spacer tube 21. After lenses 2 come into contact with extensions 24 and 25, then spacer tube 21 itself is also pressed against system tube I by the transverse force components and made to lie against it free from play.

In this embodiment as well, rod lenses 2 are seated so as to be stable and free from play. This spacer tube 21 represents a substantial improvement, especially as regards the design illustrated in FIG. 2 of document DE 2431631 C2, mentioned above.

The illustrated spacer tubes can be arranged in the system tube in pre-defined or not previously defined rotational positions, which leads to pre-defined or undefined radial positions of the rod lenses, respectively.

If the spacer tubes are put into place in a pre-defined rotational position in the system tube, it is, e.g., possible to arrange the tilting of all spacer tubes in one plane. It would be ideal if the desired pre-defined rotational positions of the spacer tubes were locked. For example, a tongue on the outer circumference of each spacer tube can engage a groove in the system tube.

The spacer tubes also can be arranged in the system tube without having a defined rotational position, however.

In the case of spacer tubes being symmetrical in an axial direction, such as spacer tubes 4 or 13, for example, the orientation of their mounting is not critical. In the case of unsymmetrical spacer tubes, such as spacer tubes 3 or 3', however, the axial orientation could be important. If, e.g., using only spacer tubes corresponding to spacer tube 3 in an undefined orientation, a rod lens could be engaged on both sides by end faces which are perpendicular to the axis of the system tube. Therefore, for this lens, stable tilting cannot be achieved. To prevent this situation, a pre-selected order of the spacer tubes, also with preselected axial orientations, should be preferred.

Spacer tubes corresponding to spacer tube 3 were used in practical tests. These spacer tubes were mounted randomly as to their axial orientation and even as to their rotational orientation. There resulted a significant reduction in the sensitivity of the telescope to sharp accelerations, i.e., shocks.

It is also possible to use several different embodiments of spacer tubes in one stack of lenses, also here the spacer tubes can be arranged in random or pre-defined positions.

What is claimed is:

1. An endoscopic telescope comprising:

a system tube (1) having all inside diameter and end holding means;

a plurality of spacer tubes (3, 3', 3", 4, 4', 13, 18, 19, 21) and rod lenses (2, 2') stacked alternatingly in said system tube between said end holding means, said rod lenses having external diameters smaller than said inside diameter of said system tube, said spacer tubes and said rod lenses being movable relative to said system tube, and said rod lenses having convex end faces abutting said spacer tubes; and spring means urging said tubes and rod lenses together between said end holding means, at least one of said spacer tubes (3, 3', 3", 4, 4', 13, 18, 19, 21) having an eccentric protruding portion on at least one axial end at an angular circumferential position to contact an adjacent convex surface of a rod lens (2, 2') whereupon said rod lens having the contacted convex surface is laterally urged out of a position coaxial with said system tube.

2. An endoscopic telescope according to claim 1 wherein said at least one spacer tube (4, 4', 13, 18, 19, 21) comprises protruding portions on both axial ends.

3. An endoscopic telescope according to claim 1 wherein all said spacer tubes (3, 3', 3", 4, 4', 13, 18, 19, 21) of the endoscope optics comprise protruding portions.

4. An endoscopic telescope according to claim 1 wherein the protruding end face of said at least one spacer tube (3, 3', 3", 4, 4', 19) is plane and inclined to its longitudinal axis.

* * * * *